United States Patent [19]

Clifton

[11] Patent Number: 4,765,180
[45] Date of Patent: Aug. 23, 1988

[54] VISCOMETER

[76] Inventor: Michael Clifton, "Willow Rise" Hall Lane, Harbury, Leamington Spa, Great Britain, CV33 9HG

[21] Appl. No.: 47,010
[22] PCT Filed: Sep. 2, 1986
[86] PCT No.: PCT/GB86/00521
  § 371 Date: Apr. 23, 1987
  § 102(e) Date: Apr. 23, 1987
[87] PCT Pub. No.: WO87/01450
  PCT Pub. Date: Mar. 12, 1987

[30] Foreign Application Priority Data
  Sep. 3, 1985 [GB] United Kingdom ............... 8521882

[51] Int. Cl.⁴ .................................... G01N 11/14
[52] U.S. Cl. ................................................ 73/59
[58] Field of Search ................................. 73/59, 60

[56] References Cited
U.S. PATENT DOCUMENTS

| | | | |
|---|---|---|---|
| 2,587,174 | 2/1952 | Lanz | 73/59 X |
| 3,533,275 | 10/1970 | Zemp | 73/59 |
| 4,175,425 | 11/1979 | Brookfield | 73/59 |
| 4,373,147 | 2/1983 | Carlson, Jr. | 73/59 X |

FOREIGN PATENT DOCUMENTS 810242  3/1959  United Kingdom .................. 73/59

Primary Examiner—Stewart J. Levy
Assistant Examiner—Joseph W. Roskos
Attorney, Agent, or Firm—David W. Gee; Erik M. Arnhem

[57] ABSTRACT

A viscometer in which the angular position of an element responsive to the viscosity of a liquid, the viscosity of which is to be monitored, is sensed by a magnetic resistive sensor adapted to supply intermittent electrical signals to an electronic means recording the angular position.

10 Claims, 3 Drawing Sheets

VISCOMETER

This invention relates to viscometers, and in particular to an improved sensing arrangement and control arrangement therefor.

The measurement of viscosity is important in many production processes, and there have been a large number of proposals for viscosity measuring apparatus.

One previous proposal is that of my own earlier United Kingdom patent application No. 2 058 341, which used a continuously rotated, resiliently mounted bob immersed in the test liquid; the change in angular position of a detection arm connected to the bob with change in liquid viscosity was recorded once each bob revolution by detector means, conveniently optical detector means.

An alternative arrangement is that disclosed in U.S. Pat. No. 4,448,061 in which a transducer is provided with a stator included in the drive of a resiliently yieldable connection subject to a constant speed drive, and having a rotor which turns relative to the stator as the connection yields or recovers in response to viscosity changes; the transducer provides a continuous signal, the strength of which changes with viscosity changes, and which is continuously delivered to a digital display or readout which is responsive thereto.

It is an object of my invention to provide a viscometer having an intermittent signal delivered to a recorder e.g. a visual display, but with an accuracy at least equal to that of known apparatus with continuously delivered signals.

Thus according to one feature of my invention I provide a viscometer in which the angular position of an element responsive to the viscosity of a test liquid is sensed by a magnetoresistive sensor. Preferably the sensor indicates the relative angular positions of two rotatable elements, one of which is responsive to the liquid viscosity. Thus I provide a viscometer for use in monitoring the viscosity of a liquid, which includes a rotatable support element, drive means to rotate said support element, a rotatable driven element coaxial with said support element and having a part which is to be immersed in a liquid the viscosity of which is to be monitored and which is to be subjected to a viscous drag which changes as the viscosity of the liquid changes, resilient means connecting the elements and which yields with variation in the relative angular position of the elements as the viscous drag increases, electrical means to sense the variation in the relative angular position of the elements and to provide an electrical output signal of a magnitude dependent upon said relative angular position, and electronic means communicating with the electrical means and arranged to record the variation in angular position characterised in that the electrical means is a magnetoresistive sensor mounted to rotate with one of the elements and responsive to magnetic flux producing means mounted to rotate with the other of the elements, in that the electronic means is connected to the electrical means by an analogue to digital converter, and in that the electronic means is a microprocessor system adapted to derive intermittent electronic signals from the electrical means by intermittent sampling of the output of the analogue to digital converter.

In order that the viscometer of the present invention can provide rapid updates of any change in viscosity, I arrange my magnetoresistive sensor to provide several indicator signals each second, usually at least 10 signals per second and conveniently 20 signals per second.

As is well known, the electrical resistance of thin ferromagnetic, layers depends on the angle between the direction of the electrical current flowing in the layers and the direction of the imposed magnetisation (the magnetoresistive effect). For my ferromagnetic layer I prefer an alloy of 80% nickel and 20% iron, since such an alloy has a significant resistance charge of between 2% and 3%, whilst having stable and repeatable characteristics over a wide temperature range; though in alternative embodiments I may use an alloy having between 70% and 90% nickel. Thus such a material is particularly useful as a sensor in my viscometer when used to record the viscosity of a liquid.

Nevertheless, though the magnetoresistive characteristics are stable and repeatable over wide temperature range, there is a square-law relationship. This can be corrected for, to provide a linear characteristic with temperature, as by use of an auxiliary magnetic field; or as by special geometric structures such as the use of a high conductivity metal e.g. gold, deposited at an angle of 45 degrees to the X or current flow axis such that an external magnetic field by the Y direction can rotate the resultant magnetisation towards the Y axis so altering the electrical resistance of the sensor.

These correction techniques, though usable in conjunction with this one feature of my invention, nevertheless introduce some complication into the apparatus, so that in accordance with a further feature of my invention I provide a viscometer which includes sensor means adapted to produce an electrical output dependent upon liquid viscosity, and computer means to which the electrical output can be fed, the computer means having an output to a viscosity recorder and having at least one input for correction means, whereby the viscosity recorder will provide a viscosity value corrected for at least one parameter. Though a magnetoresistive sensor has an output which over a significant angular range is nearly linear, for many applications a true linear output with angle is required so that one parameter will be the linearisation of this sensor characteristic to output, i.e. to provide a linear relation between spindle relative angular deflection and output; but additionally or alternatively the parameter may be one or more of temperature, spindle type, speed of rotation and the units in which the viscosity is to be recorded, as by visual display or by printed form. By providing means to program the computer means so as to correct the instrument output signal it is possible to achieve an accuracy of plus or minus 0.5% of full scale, whilst otherwise using a standard instrument, or more cheaply a "standard" instrument less manual correctors. Use of computer means speeds any necessary corrections and avoids operator errors unavoidable with repetitive human calculations.

The instrument may be in a single housing, or as separate modules e.g. sensor, display, printer etc.

Depending upon the application, a particular instrument could be required to measure viscosity using a bob rotational speed in the range from 0.3 rpm to 300 rpm. If neither auto-rangeing nor portability are required, the bob may conveniently be driven by a synchronous AC motor, with a gearbox to permit manually selected ranges for determining the bob rotational speed; for applications in which the instrument needs to auto-range or needs to be portable, then a DC motor will conveniently be used with in the auto-range model the gearbox stepping down the bob rotational speed and allowing major speed steps to be set manually, and with in the portable embodiments the gearbox providing rangechange steps as for the AC motor driven embodiments. For portability, a DC motor energised by 6 V or 12 V batteries may be adopted.

The invention will be further described by way of example with reference to the accompanying drawings, in which FIG. 1 is a schematic side elevation of a viscometer according to the invention;

The liquid 2 under test is in container 4, preferably at a specified test temperature or at a known constant temperature, but this is not essential since a rapid-response temperature probe 5 can be introduced into container 4 to monitor liquid temperature; whilst in this embodiment the container 4 has a specified volume of test liquid 2, in an alternative embodiment container 4 may be part of a liquid conduit, so that the liquid under test is continually replaced.

Figure 1:
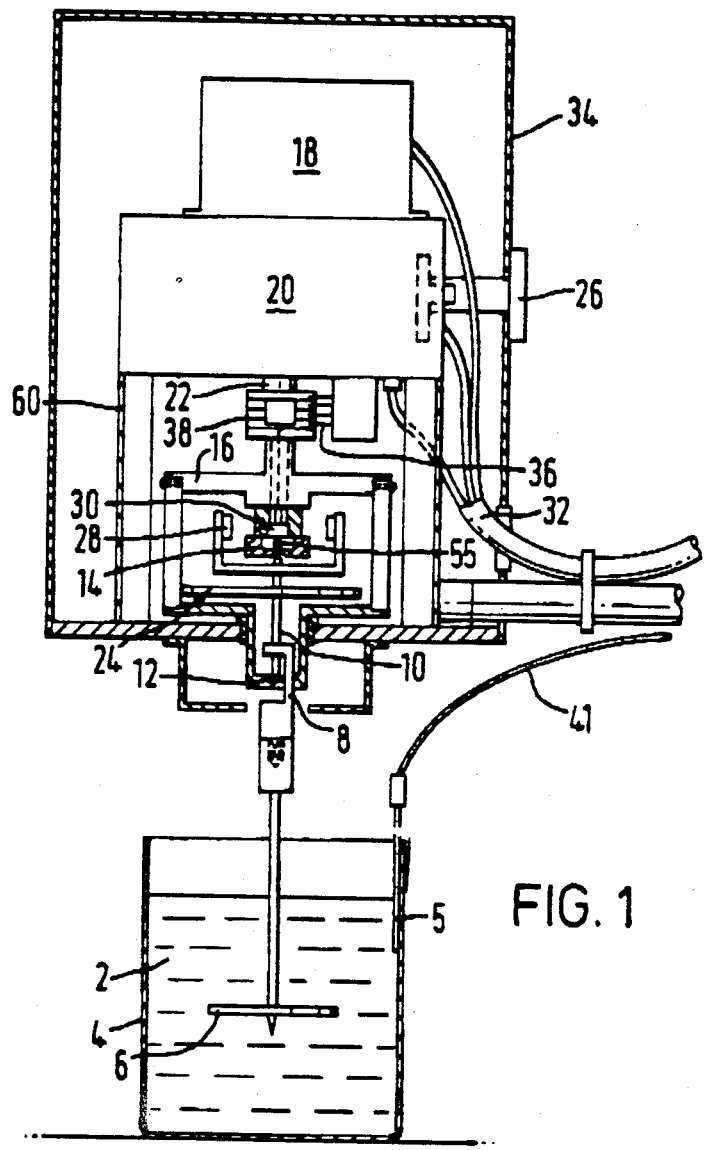

Also positioned in container 4 is a rotatable bob 6, which may be of any conventional form; in FIG. 1 the bob is shown as a disc, but in another embodiment may for instance comprise two concentric open-ended cylindrical elements, one within the other, one a driver and the other being driven by the viscous drag of the test liquid between the elements. The bob, disc and spindle may be of any convenient shape or size.

Bob 6 is suspended by lower arm 8 on upper arm 10, upper arm 10 having two needle ends and being rotatably located in needle bearings 12 and 14, in support 16. Support 16 can be rotated by motor 18 by way of gear box 20 and drive shaft 22; between support 16 and upper arm 10 is a spiral spring 24 which rotates upper arm 10 and thus bob 6, the bob 6 in this embodiment having a permitted angular displacement of up to 120 degrees relative to support 16. Means can be provided to reduce the rotational speed of support 16 should the relative angular displacement of bob 6 appear likely to exceed the specified relative angular displacement, in this embodiment by way of variable speed motor e.g. D.C., Motor 18; such means can alternatively be used to increase the rotational speed of support 16 should the relative angular displacement be too small to use fully the available range of the apparatus, that is to provide automatic rangeing in response to microprocessor signals as described below, or if preferred manual rangeing. Additionally this means can be used to maintain a constant shear stress in liquid 2. Motor 18, gear box 20 and support 16 are located within a housing 34, gear box 20 including ratio-change means 26 permitting the gearing ratio between the motor 18 and support 16 to be altered.

Figure 2:
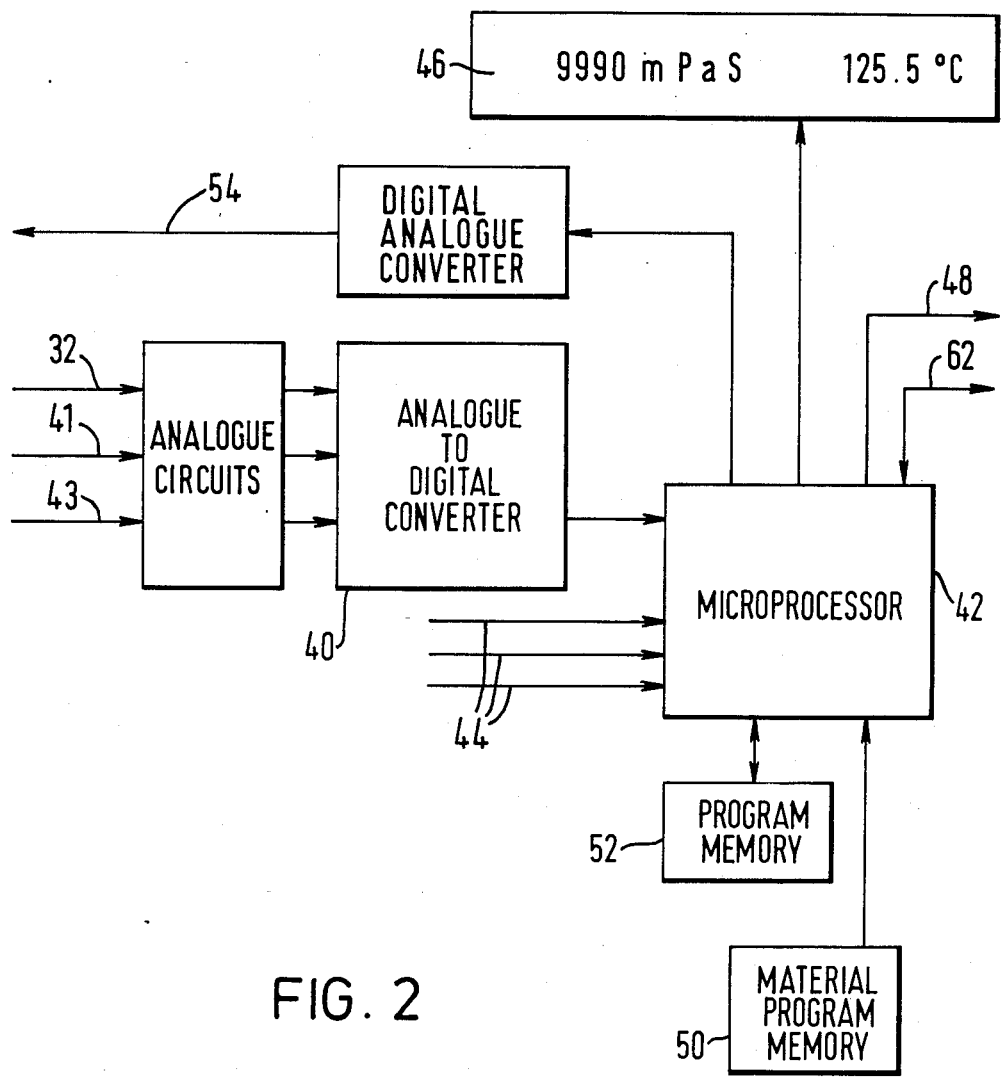
FIG. 2 is block diagram of a circuit to convert and correct electrical output signals from the viscometer of FIG. 1 to a viscosity value.
Figure 3:
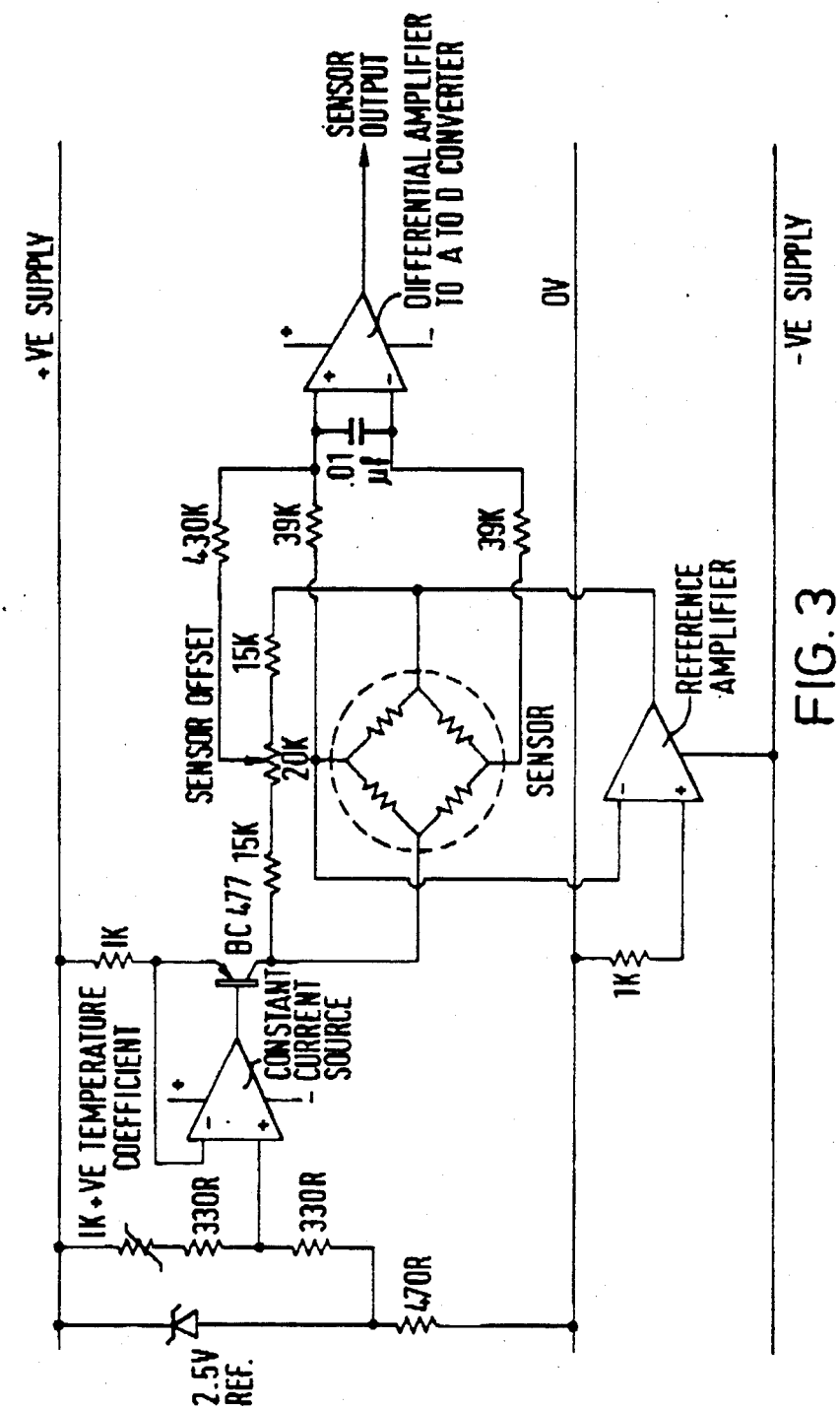
FIG. 3 is a circuit diagram for the magnetoresistive sensor.

Carried by upper arm 10 are a pair of magnets 28, between which and carried by support 16 is a magnetoresistive sensor 30. Relative angular rotational between upper arm 10 and support 16 alters the resistance of magnetoresistive sensor 30; input and output electrical lines 32 extend through housing 34 to brushes 36 engaging slip rings 38, which are electrically connected to the magnetoresistive sensor 30. As seen in FIG. 2, the other ends of electrical lines 32 are connected to the analogue to digital converter 40 and thus to microprocessor 42.

Also connected to the analogue to digital converter 40 is the electrical line 41 from the temperature probe 5, and the line 43 etc from other probes (not shown) such as one measuring that instrument temperature likely to affect the amplitude of the signal along lines 32. Also connected to the microprocessor 42 are input lines 44 applying stepped or continuously variable corrections, for instance for the spindle type and the conversion factor for the units in which the viscosity is to be recorded, e.g. displayed as by visual display 46, which in a preferred embodiment is part of the instrument; or printed by a unit connected to line 48. Preferably the viscosity measurements are made at a predetermined fixed temperature to permit ready comparison, but as an additional feature if the viscosity-temperature characteristics for the test liquid is already known this can be added to the material program memory 50 as an adjunct to program memory 52 and referred to automatically by the microprocessor for the appropriate correction factor in accordance with the input signal from probe 5.

Preferably microprocessor 42 is part of the instrument with an integral visual display unit 46 capable of both numeric and alphabetic characters correctly formatted by the microprocessor; though in an alternative embodiment the visual display unit can be remotely positioned at a more convenient location. The microprocessor 42 permits rapid yet discrete sampling, generally 10 samplings a second or above and in one embodiment at 20 samplings each second, providing speedy updating of viscosity measurement. If preferred the microprocessor can be instructed to average the readings over a given time period so that for instance the visual display does not "jitter", as a selected alternative to less frequent sampling. The fast updating can be used to control by way of output line 54 the speed of motor 18 in order to obtain automatic rangeing as mentioned above. If required the microprocessor can be instructed to display only the maximum or minimum value of the viscosity recorded during the period.

The microprocessor also permits auto-zeroing, to allow the instrument to zero itself when required. This is achieved by allowing bob 6 to rotate in air, with the microprocessor input set at "zero", so that the computer reduces any offset reading to zero using a recognised program in memory 52.

It will thus be appreciated that the viscometer of this invention permits non-linearities and temperature effects to be corrected "inside" the instrument by using a suitably programmed microprocessor and memory. The output can be displayed and/or printed in units of dynamic viscosity e.g. mPaS or in units of kinematic viscosity e.g. cSt, by taking account of the liquid specific gravity at the temperature as recorded by probe 5. Nevertheless means for manual instrument adjustment, such a sensor adjustment 55 or for correcting or trimming variations in the rate of spring 24 to compensate for manufacturing tolerances can be provided in addition to the correction allowed by the microprocessor.

It will also be appreciated that my viscometer is a torque meter, and that it can be so used.

Whilst most applications of my viscometer will make use of its high accuracy potential of better than plus or minus 0.5% of full scale, and of its frequent sampling in order to monitor rapidly any changes in the viscosity of liquid 2, it will also be appreciated that this viscometer can be used as an automatic control instrument for processes requiring a constant liquid viscosity or specific gravity achievable by altering associated process parameters or apparatus operation by way of output line 54.

Usefully the sensor will be protected from stray magnetic fields by a shield such as annular shield 60.

It will be understood that the instrument can be of unitary construction within a single housing or be "unbundled" into discrete units, perhaps widely separated as when process units are controlled or monitored from a central point. Usefully however the components shown in FIGS. 1 and 2 will together form a one-piece or "bundled" instrument. Whilst the instrument will usually have a single chip microprocessor with on-board RAM (random access memory) and I/O (input/output) circuitry such as that leading to I/O line 62, in an alternative embodiment a so-called single chip microcomputer with on-board RAM, ROM (read only memory) and I/O circuitry could be used.

I claim:

1. A viscometer for use in monitoring the viscosity of a liquid, which includes a rotatable support element, drive means to rotate said support element, a rotatable driven element coaxial with said support element and having a part which is to be immersed in a liquid the viscosity of which is to be monitored and which is to be subjected to a viscous drag which changes as the viscosity of the liquid changes, resilient means connecting the elements and which yields with variation in the relative angular position of the elements as the viscous drag increases, electrical means to sense the variation in the relative angular position of the elements and to provide an electrical output signal of a magnitude dependent upon said relative angular position, and electronic means communicating with the electrical means and arranged to record the variation in angular position characterised in that the electrical means is a magnetoresistive sensor mounted to rotate with one of the elements and responsive to magnetic flux producing means mounted to rotate with the other of the elements, in that the electronic means is connected to the electrical means by an analogue to digital converter, and in that the electronic means is a microprocessor system adapted to derive intermittent electronic signals from the electrical means by intermittent sampling of the output of the analogue to digital converter.

2. A viscometer according to claim 1 in which the electronic means is adapted to derive at least 10 signals each second.

3. A viscometer according to claim 1 in which the magnetoresistive sensor includes a ferromagnetic layer of an alloy having between 70% and 90% nickel, preferably 80% nickel and 20% iron.

4. A viscometer according to claim 1 characterised in that the electronic means includes computer means to which the electrical signals are supplied, the computer means having an output to a viscosity recorder and having at least one input for correction means so that the viscosity recorder can provide a viscosity value corrected for at least one parameter.

5. A viscometer according to claim 4 characterised in that the parameter is the variation in angular position so that the output to the viscosity recorder provides a viscosity value representative of a linear relation between variation in angular position and signal amplitude.

6. A viscometer according to claim 4 characterised in that the viscosity recorder is a visual display unit and printer combination.

7. A viscometer according to claim 1 characterised in that the drive means can rotate said support element at a speed in the range 0.3 rpm to 300 rpm.

8. A viscometer according to claim 1 characterised in that the drive means is a synchronous AC electric motor connected to a manually-charged gearbox.

9. A viscometer according to claim 1 characterised in that the drive means is a DC electric motor connected to a gearbox adapted to provide an auto-range facility.

10. A viscometer according to claim 1 characterised in that the relative angular position is up to 120°.

* * * * *